(12) United States Patent
Dannoritzer

(10) Patent No.: US 9,044,208 B2
(45) Date of Patent: Jun. 2, 2015

(54) SURGICAL INSTRUMENT

(76) Inventor: Axel Dannoritzer, Baden-Wuertt (DE)

( * ) Notice: Subject to any disclaimer, the term of this patent is extended or adjusted under 35 U.S.C. 154(b) by 0 days.

(21) Appl. No.: 13/820,816

(22) PCT Filed: Aug. 31, 2011

(86) PCT No.: PCT/EP2011/004382
§ 371 (c)(1),
(2), (4) Date: Mar. 5, 2013

(87) PCT Pub. No.: WO2012/031712
PCT Pub. Date: Mar. 15, 2012

(65) Prior Publication Data
US 2013/0253482 A1 Sep. 26, 2013

(30) Foreign Application Priority Data
Sep. 10, 2010 (DE) .......... 10 2010 044 982

(51) Int. Cl.
*A61B 17/00* (2006.01)
*A61B 19/00* (2006.01)
*A61B 17/29* (2006.01)

(52) U.S. Cl.
CPC ....... *A61B 17/00234* (2013.01); *A61B 19/2203* (2013.01); *A61B 2017/292* (2013.01); *A61B 17/29* (2013.01); *A61B 2019/2242* (2013.01); *A61B 19/22* (2013.01); *A61B 17/2909* (2013.01); *A61B 2017/00477* (2013.01); *A61B 2017/2946* (2013.01); *A61B 2019/4868* (2013.01)

(58) Field of Classification Search
CPC ............... A61B 19/22; A61B 19/2203; A61B 2019/2242; A61B 17/29; A61B 17/2909; A61B 2017/292; A61B 17/00234; A61B 2017/00477; A61B 2017/2946; A61B 2019/4868
USPC ...................................... 606/1, 205
See application file for complete search history.

(56) References Cited

U.S. PATENT DOCUMENTS

| 5,472,439 A | 12/1995 | Hurd |
| 5,584,844 A | 12/1996 | Weisshaupt |
| 5,618,308 A | 4/1997 | Holmes et al. |

(Continued)

FOREIGN PATENT DOCUMENTS

| DE | 43 16 768 A1 | 11/1994 |
| DE | 296 19 246 U1 | 1/1997 |

(Continued)

OTHER PUBLICATIONS

German Search Report issued from the German Patent Office mailed Apr. 13, 2011 for the corresponding German patent application No. 10 2010 044 982.2 (with partial English translation).

(Continued)

*Primary Examiner* — Lynsey Crandall
*Assistant Examiner* — Sebastian X Lukjan
(74) *Attorney, Agent, or Firm* — Posz Law Group, PLC

(57) ABSTRACT

The invention relates to a surgical instrument, in particular a minimally invasive surgical instrument, with a working unit, and with a control unit which has two control elements that can be separated from each other for cleaning and/or disinfection.
It is proposed that the surgical instrument has a connecting device, which is provided for connecting the working unit and the control unit to each other in such a way that they can be separated for cleaning and/or disinfection.

17 Claims, 7 Drawing Sheets

(56) References Cited

U.S. PATENT DOCUMENTS

2004/0230221 A1    11/2004   Gadberry et al.
2011/0306952 A1 *  12/2011   Chen et al. .................. 606/1

FOREIGN PATENT DOCUMENTS

| DE | 198 19 382    C1 | 8/1999  |
|----|------------------|---------|
| DE | 694 19 996    T2 | 2/2000  |
| DE | 20 2004 015 642 U1 | 12/2004 |
| DE | 20 2009 002 235 U1 | 7/2009  |
| WO | 97/24072      A1 | 7/1997  |

OTHER PUBLICATIONS

International Search Report of the International Searching Authority mailed Dec. 12, 2011 for the corresponding international application No. PCT/EP2011/004382 (with partial English translation).

Written Opinion of the International Searching Authority mailed Mar. 5, 2012 for the corresponding international application No. PCT/EP2011/004382 (with partial English translation).

* cited by examiner

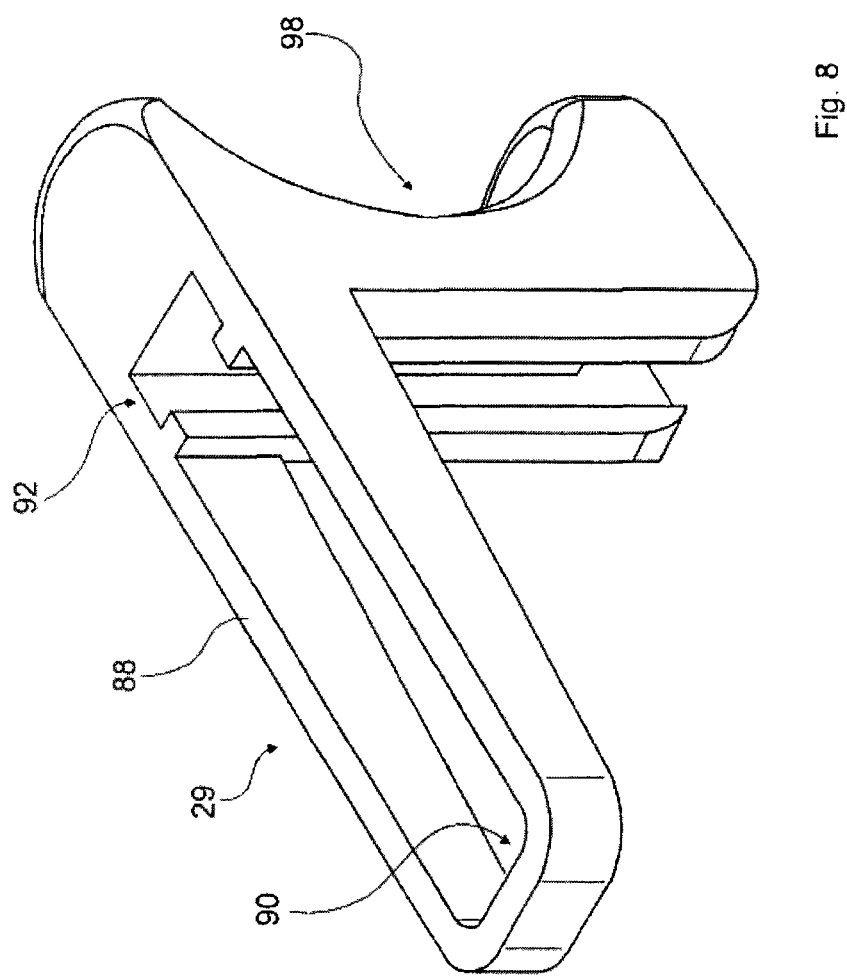

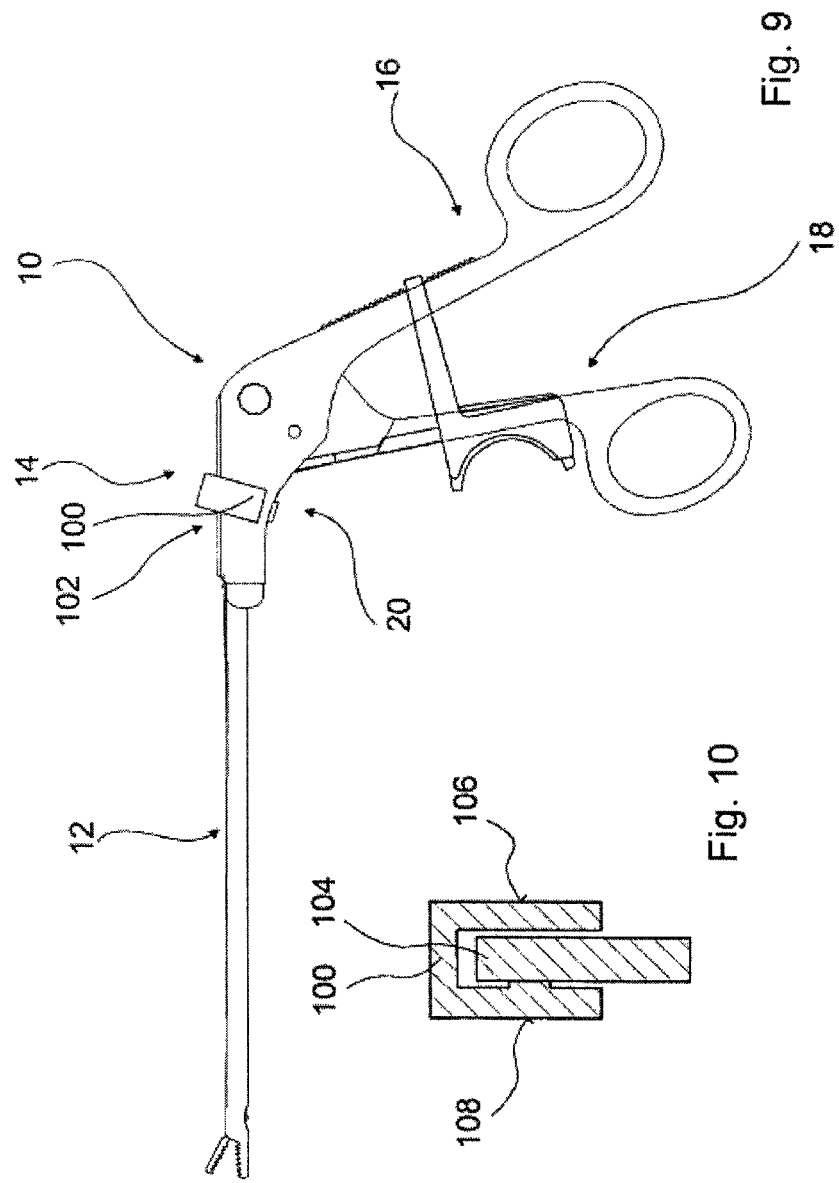

SURGICAL INSTRUMENT

CROSS REFERENCE TO RELATED APPLICATIONS

This application is a U.S. national stage application of PCT/EP2011/004382 filed on Aug. 31, 2011, and claims priority to, and incorporates by reference, German patent application No. 10 2010 044 982.2 filed on Sep. 10, 2010.

TECHNICAL FIELD

The invention relates in particular to a surgical instrument.

BACKGROUND

A surgical instrument, in particular a minimally invasive surgical instrument, with a working unit, and with a control unit which has two control elements that can be separated from each other for cleaning and/or disinfection, has already been proposed.

SUMMARY

The invention relates to a surgical instrument, in particular a minimally invasive surgical instrument, with a working unit, and with a control unit which has two control elements that can be separated from each other for cleaning and/or disinfection.

It is proposed that the surgical instrument has a connecting device, which is provided for connecting the working unit and the control unit to each other in such a way that they can be separated for cleaning and/or disinfection. A "surgical instrument" is to be understood in particular as an instrument that is provided for surgical procedures deemed appropriate by a person skilled in the art and, advantageously, for a minimally invasive surgical procedure. For minimally invasive operations, the instrument has a shaft area between a working means of the working unit and the control unit, which shaft area has the smallest possible maximum diameter perpendicular to a main direction of extent, advantageously less than 8 mm, particularly advantageously less than 5 mm. The shaft area preferably has this small diameter along the entire length in the main direction of extent. In a state ready for operation, the shaft area between a working means and a control unit is preferably more than 50 mm in length, advantageously more than 70 mm in length, particularly advantageously more than 100 mm in length. "Minimally invasive" is to be understood in particular as suitable for laparoscopy, thoracoscopy, endoscopic operations, other minimally invasive operations deemed appropriate by a person skilled in the art. The surgical instrument can perform various functions that are deemed appropriate by a person skilled in the art, in particular a scissors function and/or advantageously a forceps function. Various forms of forceps and/or scissors are known to a person skilled in the art. A "control unit" is to be understood in particular as a unit provided for absorbing a mechanical force exerted by an operator, wherein the shaft area conveys the force onward to the working means. The control unit preferably has two control elements which are mounted so as to be pivotable with respect to each other and which are preferably provided for being gripped by an operator. The control unit preferably has a handle configuration akin to scissors handles and/or forceps handles. "Provided" is to be understood in particular as specially equipped and/or designed. A "working unit" is to be understood in particular as a unit that can be connected to the control unit and that has the working means. The working unit is preferably provided for being at least partially inserted through a skin opening into a surgical site, particularly in a minimally invasive operation. The term "control element" is to be understood in particular as an element having at least one grip area, which is provided for being actuated by an operator in a working procedure. The phrase "can be separated from each other for cleaning and/or disinfection" is to be understood in particular as meaning that at least the working unit and the control elements can each be arranged spatially separate from each other for cleaning and/or disinfection. A "connecting device" is to be understood in particular as a device which is provided for firmly connecting the working unit and the control unit with a force fit and/or advantageously a form fit. The connecting device preferably latches the working unit and the control unit to each other. The phrase "to connect to each other" is to be understood in particular as meaning that the connecting device prevents a movement of the entire working unit relative to the entire control unit.

By virtue of the design of the surgical instrument according to the invention, particularly advantageous cleaning and/or disinfection can be achieved using a simple construction. Moreover, a particularly flexible surgical instrument can be made available in which the control unit can be combined with different working units.

In a further embodiment, it is proposed that the connecting device is provided for connecting the working unit and the control unit in such a way that they can be separated without use of tools, as a result of which the surgical instrument can be disassembled particularly conveniently and quickly for cleaning and/or disinfection and for replacement of the working unit. The phrase "can be separated without use of tools" is to be understood in particular as meaning that the connection between the working unit and the control unit is designed to be releasable manually by an operator, that is to say the operator does not require any auxiliary means to release the connection.

It is also proposed that the connecting device has at least one latch element and a spring element which is provided for exerting a force on the latch element, as a result of which particularly convenient disassembly is possible using a simple construction. A "latch element" is to be understood in particular as an element which is provided for exerting a connecting force in a form-fit connection. The latch element is preferably mounted movably for releasing the form-fit connection. A "spring element" is to be understood in particular as a torsion spring, bending spring, tension spring and/or gas spring deemed appropriate by a person skilled in the art. The spring element is advantageously designed as a compression spring. The spring element is particularly advantageously designed as a helical spring.

It is further proposed that the working unit has at least one movement stop, which is provided for arranging the control elements undetachably with respect to each other, as a result of which, during use, unwanted separation can be avoided and, in this way, particularly comfortable usage can be achieved. A "movement stop" is to be understood in particular as a structure and/or arrangement which is provided for preventing at least one movement by an opposing force. The phrase "arranging the control elements undetachably with respect to each other" is to be understood in particular as meaning that the movement stop, in a state ready for operation, prevents the control elements from being alignable with respect to each other in such a way that a form-fit connection between the two control elements is releasable. Thus, the movement stop of the working unit is a part of the form-fit connection between the two control elements.

It is also proposed that the control unit has a slotted guide, which guides the control elements at least in a working movement. A "slotted guide" is to be understood in particular as a guide in which a raised part, in particular a pin, is mounted in a depression, particularly in a channel, and is guided at least by side walls of the depression. The term "working movement" is to be understood in particular as a movement that causes an actuation of the working means. The slotted guide permits a particularly high degree of stability and a structurally very simple and separable connection between the control unit and the working unit.

It is further proposed that the surgical instrument comprises a locking device, which is provided for exerting a locking force between the control elements. A "locking device" is to be understood in particular as a device which, in at least one operating state, prevents a movement of the working means in at least one direction. The locking device preferably prevents a movement of the control elements relative to each other in at least one direction. The locking device permits particularly comfortable working with the surgical instrument. The locking device is, in an operating state, preferably secured with a form fit by the control elements.

It is further proposed that the locking device is secured in such a way that it can be separated from the control elements, without use of tools, for cleaning and/or disinfection, as a result of which particularly efficient and convenient cleaning and/or disinfection can be achieved.

It is also proposed that the connecting device has at least one unlocking control means, which is at least partially arranged on a side of the control unit, which side faces away from the control elements, as a result of which a particularly comfortable actuation of the unlocking control means is possible. An "unlocking control means" is to be understood in particular as a means whose actuation at least initiates a separation of the working unit and the control units. An actuation of the unlocking control means preferably releases a lock between the working unit and the control units. A "side of the control unit averted from the control elements" is to be understood in particular as a side of the control unit which, seen from at least one point of the control elements, is arranged behind a joint of the control units. The control unit and at least one of the control elements are preferably situated on a straight line which, in at least one operating state, intersects the joint between the control unit and said control element.

The invention further relates to a working unit of a surgical instrument, in particular of a minimally invasive surgical instrument, with a shaft and a push and pull element, both of which are movable relative to each other.

It is proposed that the working unit of the surgical instrument has a connecting element, which is provided for arranging the shaft and the push and pull element undetachably with respect to each other. A "shaft" is to be understood in particular as an element of the working unit, which connects at least one area and/or an element of a working means of the working unit, in particular a joint axle, mechanically and firmly to a connecting area. In a state ready for operation, the connecting area is advantageously directly and firmly connected to a control unit. A "push and pull element" is to be understood in particular as an element of the working unit that transfers a working movement from the control unit to the working means. The push and pull element preferably transfers the working movement through a shaft area. The term "connecting element" is to be understood in particular to mean an element which is provided for preventing at least one movement of the push and pull element relative to the shaft by an opposing force. The phrase "arranging the control elements undetachably with respect to each other" is to be understood in particular as meaning that the connecting element, in a state separate from the control unit in particular, prevents the shaft and the push and pull element from being alignable with respect to each other in such a way that a form-fit connection between the shaft and the push and pull element is releasable. Thus, the connecting element is a part of a form-fit connection between the shaft and the push and pull element. The undetachable arrangement of the shaft and of the push and pull element preferably means that all the other parts of the working unit are also arranged undetachably.

By virtue of the design of the working unit of the surgical instrument according to the invention, particularly good cleaning and/or disinfection can be achieved together with a high level of convenience, and it is possible to avoid the loss of individual components, in particular small components of the working means.

In an advantageous embodiment of the invention, it is proposed that the connecting element is formed at least partially by a spring. Alternatively and/or in addition, the connecting element could be formed at least partially by a flap and/or hinge device. A "spring" is to be understood in particular as a torsion spring, bending spring, tension spring and/or gas spring deemed appropriate by a person skilled in the art. The connecting element is advantageously formed at least partially by a leaf spring. By means of the spring, it is advantageously possible to dispense, on one side of the connecting element, with a movable connection between the connecting element and the shaft and/or the push and pull element. In this way, it is possible to reduce design work and costs.

It is further proposed that the connecting element is firmly connected to the shaft and/or to the push and pull element, thereby achieving low costs and minimal design work. The phrase "firmly connected" is to be understood in particular as meaning connected at least partially immovably relative to each other. The connecting element is advantageously integrally bonded to the shaft and/or to the push and pull element.

It is further proposed that the shaft and/or the push and pull element has an at least partially T-shaped groove which, in at least one operating state, at least partially guides the connecting element. A "T-shaped groove" is to be understood in particular as a groove with two undercuts. Alternatively or in addition, the shaft and/or the push and pull element could have an L-shaped groove and/or a different groove deemed appropriate by a person skilled in the art. In this context, "guide" is to be understood in particular as meaning that the groove is provided for exerting a force on the connecting element in at least one direction, advantageously in all directions, perpendicular to a main direction of extent of the groove. By means of the T-shaped groove, it is possible to achieve low costs and minimal design work.

It is also proposed that the push and pull element is mounted in such a way that it can be pivoted at least partially out of the shaft, as a result of which the working unit can be particularly advantageously cleaned and/or disinfected. The phrase "can be pivoted at least partially out of the shaft" is to be understood in particular as meaning that the push and pull element is movable about a rotation axis, relative to the shaft, into a position in which at least one area of the push and pull element, in a direction perpendicular to a main direction of extent of the shaft, is arranged spaced apart from each portion of the shaft by more than 2 mm, advantageously more than 10 mm.

The invention further relates to a method for assembling a surgical instrument, in particular a minimally invasive surgical instrument, with a working unit, a control unit and a connecting device which has at least one latch element and an unlocking control means, wherein the latch element is provided for latching the working unit with the control unit, wherein the latch element is introduced into the control unit, and then the unlocking control means is firmly connected to the control unit. The term "assembling" is to be understood in particular as joining together in a production of the surgical instrument. "Assembling" is not to be understood as components being joined together by an operator. An "unlocking control means" is to be understood in particular as a means which is provided in the connecting device for releasing a connection between the working unit and the control unit when actuated by an operator. The term "introduced" is to be understood in particular as meaning that the latch element is pushed into the control unit and, in at least one operating state, is supported by the control unit so as to be displaceable in two parallel directions. Advantageously, the latch element is integrally bonded to the control unit. Alternatively or in addition, the latch element and the control unit can be connected to each other with a force fit or form fit. By the method according to the invention, it is possible to obtain, with a simple design, a particularly stable connecting device that is comfortable to use and that has surfaces which can be particularly effectively cleaned and/or disinfected.

It is further proposed that the connecting device has a spring element and a closure element, wherein the spring element and the closure element are introduced into the control unit and the closure element is firmly connected to the control unit, thereby achieving surfaces that can be particularly effectively cleaned and/or disinfected. A "closure element" is to be understood in particular as an element which is provided for closing an opening of the control unit. The closure element preferably closes the opening through which the latch element and the spring element are introduced into the control unit. Advantageously, the closure element is integrally bonded to the control unit. Alternatively, the closure element and the control unit can be connected to each other with a force fit or form fit.

BRIEF DESCRIPTION OF THE DRAWINGS

Further advantages will become clear from the following description of the drawing. The drawing depicts two embodiments of the invention. The description and the claims contain numerous features in combination. A person skilled in the art will also consider the features individually, where appropriate, and combine them to form other meaningful combinations.

FIG. 8 is a perspective view of a connecting device of the surgical instrument from FIG. 1, FIG. 9 is a view of an alternative embodiment of an unlocking control means of a surgical instrument from FIG. 1, and FIG. 10 a sectional view through the alternative embodiment of the unlocking control means from FIG. 9.

DETAILED DESCRIPTION

Figure 1:
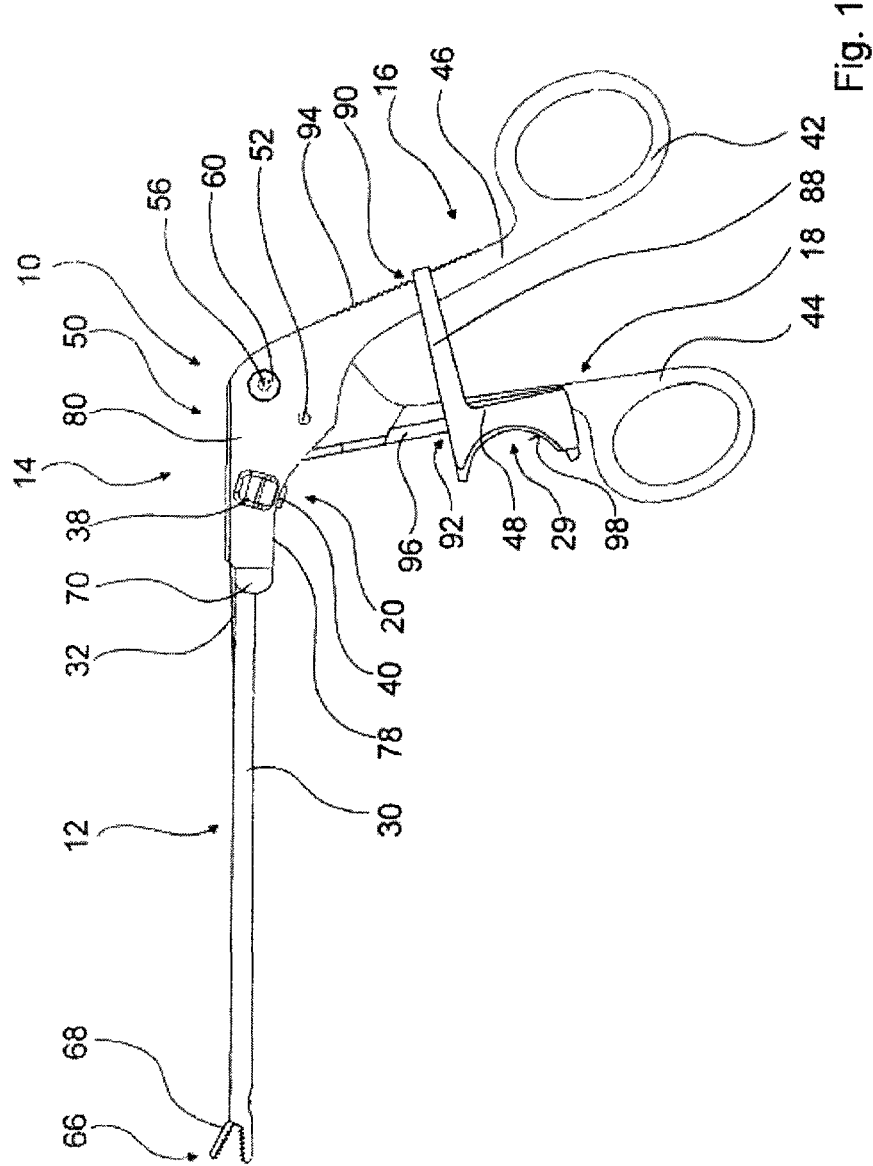
FIG. 1 is a view of a surgical instrument ready for operation, with a working unit, a control unit and a connecting device.
Figure 2:
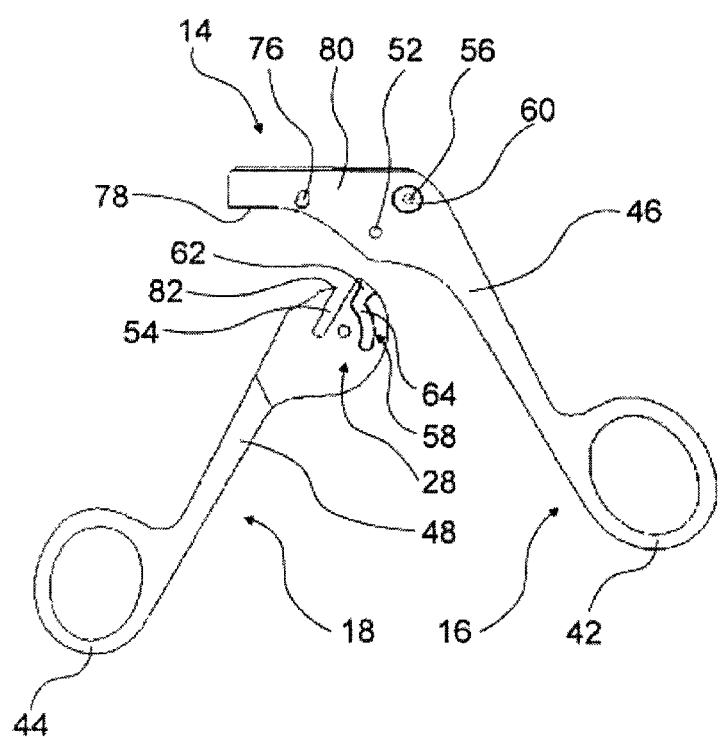
FIG. 2 is a view of the control unit of the surgical instrument from FIG. 1 with two control elements arranged separately from each other.

FIG. 1 shows a surgical instrument 10 designed according to the invention, which is implemented as a minimally invasive surgical instrument, with a working unit 12 and a control unit 14. The control unit 14 is designed in the manner of scissor handles. As FIG. 2 shows, the control unit 14 has a first control element 16 and a second control element 18, both of which are connected in such a way that they can be separated from each other for cleaning and/or disinfection. The control elements 16, 18 each have a grip area 42, 44. The grip areas 42, 44 are ring-shaped. In this way, an operator (not shown) can exert a force in different directions on the grip areas 42, 44.

The grip areas 42, 44 are each connected to a joint 50 by a web 46, 48 of the control elements 16, 18. In a state ready for operation, the webs always have an angle, with respect to a main direction of extent of the working unit 12, of greater than 45 degrees. The joint 50 has a slotted guide 28 and a joint axle 52. The joint axle 52 is integrally bonded to the first control element 16. The second control element 18 has a recess 54, into which the joint axle 52 can be inserted by an operator when joining the components together, that is to say in particular after cleaning and/or disinfection. The recess 54 extends parallel to the web 48 of the second control element 18. In a state ready for operation, the joint axle 52 comes to lie on an inner end of the recess 54.

The slotted guide 28 has a pin 56 and a channel 58. The pin 56 has a base 60, which is welded to the first control element 16. The pin 56 extends into a joint area of the joint 50. The channel 58 is introduced into the second control element 18. It has an insertion area 62 and a working area 64. The working area 64 extends in a semicircle around the inner end of the recess 54. The insertion area 62 extends parallel with respect to the recess 54.

In a certain orientation of the control elements 16, 18 to each other as shown in FIG. 2, the joint axle 52 and the pin 56 can be inserted into the recess 54 and into the insertion area 62 of the channel 58 in a direction parallel with respect to the recess 54. After the insertion, the control elements 16, 18 are pivotable, relative to each other, about the joint axle 52. In so doing, the pin 56 runs in the working area 64 of the channel 58. When the pin 56 is arranged in the working area 64, this arrangement prevents the control elements 16, 18 from being separable in a direction parallel to the recess 54, that is to say without previous pivoting. The control elements 16, 18 are separable only in the orientation shown in FIG. 2.

Figure 3:
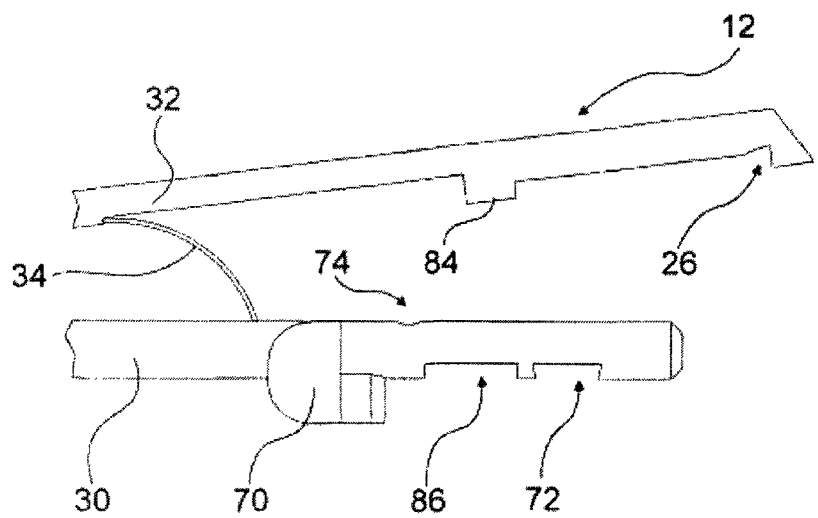
FIG. 3 is a partial view of the working unit of the surgical instrument from FIG. 1.
Figure 4:
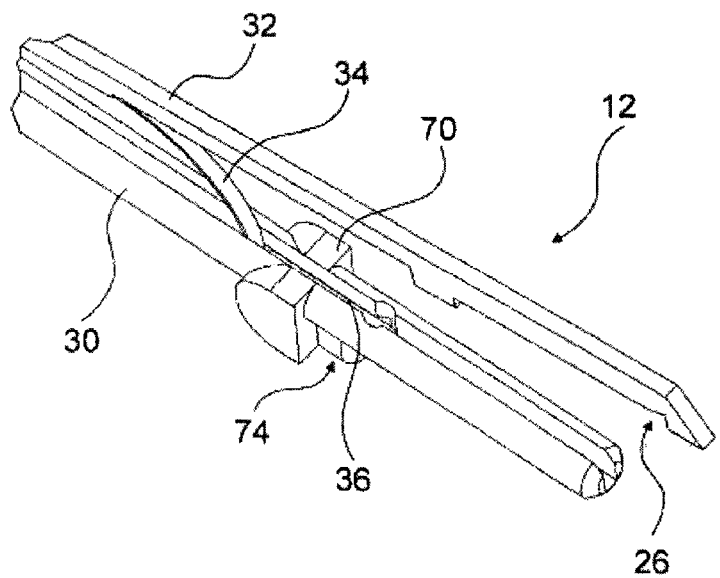
FIG. 4 is a partial perspective view of the working unit of the surgical instrument from FIG. 1.

The working unit 12 shown in more detail in FIGS. 3 and 4 has a shaft 30, a push and pull element 32 and a working means 66. In a state ready for use, the shaft 30 is connected mechanically firmly to the control unit 14, namely to the first control element 16 of the control unit 14. The working means 66 is implemented as a forceps means, more precisely as a crocodile-jaw-shaped working means. It is partially designed in one piece with the shaft 30. A part 68 of the working means 66 is movable relative to the shaft 30 and to the push and pull element 32. This part 68 is connected operatively to the push and pull element 32.

For connection to the control unit 14, the shaft 30 has a stop 70 and a latch recess 72. The stop 70 is designed as a thickening of the shaft 30 perpendicular to a main direction of extent of the shaft 30. In a state ready for operation, the stop 70 prevents a movement of the working unit 12 in the direction of the control unit 14. A latch element 22 engages in the latch recess 72 and, in a state ready for operation, prevents a movement of the working unit 12 in a direction away from the control unit 14. The latch recess 72 is arranged in a connecting area 74 of the working unit 12. The connecting area 74 is provided for being inserted into the control unit 14 in the main direction of extent of the shaft 30.

The shaft area of the working unit 12 is arranged between the stop 70 and the working means 66. The shaft 30 has a groove 36 along its main direction of extent. The groove 36 is provided for movably supporting the push and pull element 32 relative to the shaft 30. The shaft 30 and the push and pull element 32 are connected operatively to the working means 66. The push and pull element 32 is supported such that it can be pivoted partially out of the shaft 30, about an axis arranged on the working means 66. The push and pull element 32 is implemented as a push and pull rod.

The working unit 12 has a connecting element 34. The connecting element 34 connects the shaft 30 and the push and pull element 32 on a side of the shaft 30 directed away from the working means 66. Herein the connecting element 34 prevents the push and pull element 32 from being pivotable relative to the shaft 30 by more than 10 degrees. In this way, the connecting element 34 prevents a movement of the push and pull element 32 relative to the shaft 30, which releases a form-fit connection between the shaft 30, the push and pull element 32 and the movable part 68 of the working means 66. The connecting element 34 thus arranges the shaft 30 and the push and pull element 32 undetachably with respect to each other. In a state ready for operation, the connecting element 34 is arranged in the groove 36 between the shaft 30 and the push and pull element 32.

The connecting element 34 is formed by a leaf spring and is welded to the push and pull element 32. The groove 36 of the shaft 30 has a T-shaped design in an area of the stop 70. The connecting element 34 has two wings (not shown) which engage in the T-shaped groove 36. The wings guide the connecting element 34 movably in the main direction of extent of the shaft 30. In assembly, the connecting element 34 is first of all inserted into the T-shaped groove 36 and then welded to the push and pull element 32. Herein the connecting element 34 is arranged such that it is too short to be slid out of the groove 36.

Figure 5:
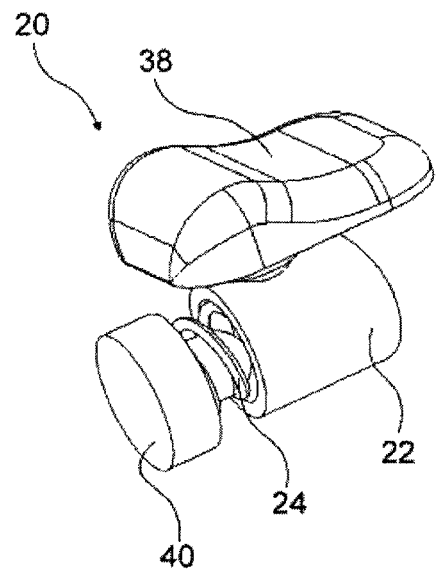
FIG. 5 is a perspective view of the connecting device of the surgical instrument from FIG. 1.
Figure 6:
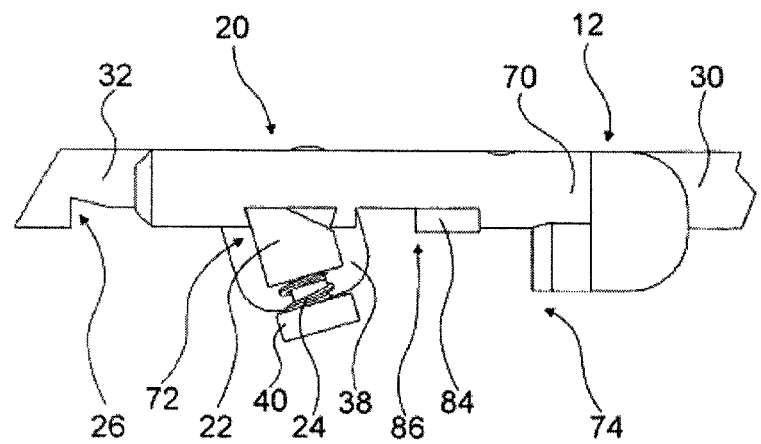
FIG. 6 is a view of the working unit and the connecting device of the surgical instrument from FIG. 1 in a latched operating state.
Figure 7:
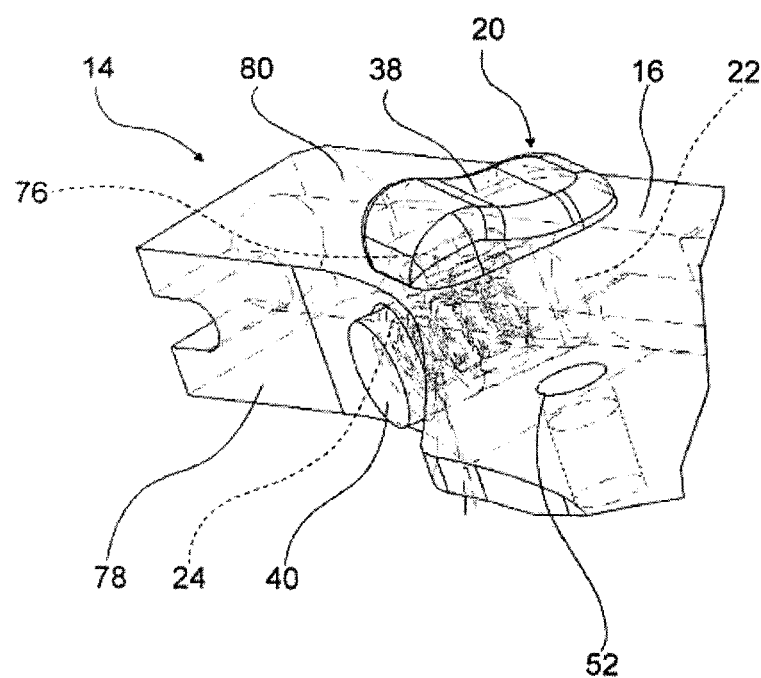
FIG. 7 is a partial perspective view of the control unit and the connecting device of the surgical instrument from FIG. 1.

The control unit 14 has a connecting device 20 depicted in FIGS. 5, 6 and 7. The connecting device 20 has the latch element 22 which, in a state ready for operation, latches the working unit 12 and the control unit 14 to each other such that they can be separated, without use of tools, for cleaning and/or disinfection. For this purpose, the connecting device 20 has a spring element 24, an unlocking control means 38 and a closure element 40. The spring element 24 is implemented as a compression spring, specifically as a helical spring. It is arranged between the latch element 22 and the closure element 40. The spring element 24 exerts a force on the latch element 22, which force locks the latch element 22 to the working unit 12, specifically to the recess 54 of the shaft 30, when the working unit is pushed into the control unit 16. For this purpose, the latch element 22 is mounted in a movement direction that has an angle of 74 degrees with respect to the main direction of extent of the shaft 30. Self-actuated release of the connection is ruled out in this way. Moreover, the latch element 22 has an oblique surface which, when the working unit 12 is pushed into the control unit 14, unlocks the latch element 22, that is to say pushes it aside. When the working unit 12 is in a position ready for operation relative to the control unit 14, the latch element 22 latches automatically.

In assembly of the working unit 12 of the surgical instrument 10, the latch element 22 is first of all inserted into a recess of the first control element 16. The recess is designed as a bore. Furthermore, the recess is arranged on a narrow side 78 of the first control element 16 and faces toward the second control element 18. The unlocking control means 38 is then placed onto the latch element 22 through a recess 76 arranged on a broad side 80 of the first control element 16 and is welded to the latch element 22 by means of a laser. Thereafter, the spring element 24 and the closure element 40 are introduced into the recess on the narrow side 78. Then the closure element 40 is welded to the first control element 16. The weld point is then polished.

The push and pull element 32 of the working unit 12 has a movement stop 26, which is connected operatively to the second control element 18. For this purpose, the movement stop 26 hooks onto an edge 82 of the second control element 18. During a movement of the second control element 18, the edge 82 moves the push and pull element 32 in the main direction of extent of the push and pull element 32. The push and pull element 32 has a stop 84, which engages in a recess 86 of the shaft 30. In a state ready for operation, the stop 84 limits a movement clearance of the push and pull element 32 relative to the shaft 30 in the main direction of extent of the shaft 30. Herein, in a state ready for operation, the stop 84 prevents a movement of the control elements 16, 18 to each other, which movement moves the pin 56 into the insertion area 62. Thus, the movement stop 26 arranges the control elements 16, 18 undetachably with respect to each other in a state ready for operation.

As is shown in FIGS. 1 and 8, the surgical instrument has a locking device 29. In a locked operating state, the locking device 29 exerts a locking force between the control elements 16, 18. The locking device 29 prevents a movement of the control elements 16, 18 in a direction which is counter to a direction in which an operator exerts a force on the control elements 16, 18. The locking device 29 has an annular area 88 which, in a state ready for operation, partially encompasses the control elements 16, 18. The annular area 88 has a substantially rectangular design. Two inner faces 90, 92 of the annular area 88 exert the locking force. For this purpose, one inner face 90 engages in a row of teeth 94 of the first control element 16. The other inner face 92 encompasses a T-shaped groove 96 of the second control element 18. The locking device 29 is mounted slidably on this groove 96. Moreover, the locking device 29 has a control area 98. The control area 98 has a concave shape, specifically the shape of part of a circle. The control area 98 is arranged on a side of the annular area 88 on which the inner face 90 is arranged that encompasses the T-shaped groove 96.

The locking device 29 is secured to the control elements 16, 18 such that they can be separated, without use of tools, for cleaning and/or disinfection. The control elements 16, 18 secure the locking device 29, with a form fit, between the grip areas 42, 44 and the joint 50 or the connecting device 20. When the first control element 16 is separated from the second control element 18, the locking device 29 is separable from the control elements 16, 18.

When assembling the surgical instrument 10, the second control element 18 is first of all inserted into the first control element 16 in the orientation shown in FIG. 2. The second control element 18 is then pivoted as far as possible in a direction of the first control element 16, that is to say the webs 46, 48 are pivoted toward each other. Thereafter, the working unit 12 is inserted into the first control element 16. Herein the second control element 18 pivots through approximately 45 degrees in a direction of the orientation shown in FIG. 2. In order to achieve the orientation shown in FIG. 2, the second control element 18 would have to be pivoted through approximately 50 degrees. This is prevented, however, by the movement stop 26.

FIGS. 9 and 10 show another embodiment of the invention. The following descriptions and the drawings are basically limited to the differences between the embodiments. With regard to identically designated components, in particular with regard to components having the same reference numerals, reference may also be made in principle to the drawings and/or the description of the other embodiment, in particular as shown in FIGS. 1 to 8.

FIGS. 9 and 10 show a further embodiment of a surgical instrument 10 according to the invention with a working unit 12 and a control unit 14 and a connecting device 20. The control unit 14 has two control elements 16, 18 that can be separated from each other for cleaning and/or disinfection. The connecting device 20 connects the working unit 12 and the control unit 14 to each other such that they can be separated for cleaning and/or disinfection. The connecting device 20 has an unlocking control means 100. The unlocking control means 100 is arranged partially on a side 102 of the control unit 14, which side faces away from the control elements 16, 18. The unlocking control means 100 is U-shaped. It encompasses a part 104 of the control unit 14. Thus, the unlocking control means 100 is provided to be actuated by pressing it, with a finger, partially in a direction of the part 104 of the control unit 14 and by gripping it with two fingers on two mutually opposite sides facing away from the part 104 of the control unit 14.

The invention claimed is:

1. A surgical instrument, comprising a control unit having two control elements that can be separated from each other for cleaning, a working unit, and a connecting device detachably connecting the working unit and the control unit to each other,
the working unit having a shaft and a push-pull element, the shaft of the working unit including a recess, and the push-pull element of the working unit including first and second stops,
the surgical instrument including the working unit, the control unit, the two control elements of the control unit and the connecting device being configured to assemble and disassemble manually and without the use of tools between an operating state ready for performing surgery and a disassembled state for cleaning;
in the operating state the working unit, the control unit, the two control elements of the control unit and the connecting device are assembled together into the surgical instrument for performing surgery, and
in the disassembled state the working unit and the control unit are dismantled and separated from each other and the two control elements are dismantled and separated from each other for cleaning,
wherein the first stop of the push-pull element of the working unit is arranged together with the control elements into a form-fit connection when assembled in the operating state, the form-fit connection limiting movement of the two control elements relative to each other and preventing the two control elements from becoming oriented relative to each other at an orientation permitting release of the two control elements from the form-fit connection, and
wherein the form-fit connection includes the second stop of the push-pull element engaging the recess of the shaft resulting in the form-fit connection limiting a movement clearance of the push-pull element relative to the shaft in a main direction of the shaft.

2. The surgical instrument as claimed in claim 1, wherein the connecting device has at least one latch element and a spring element which is provided for exerting a force on the latch element.

3. The surgical instrument as claimed in claim 1, wherein the control unit has a slotted guide, which guides the control elements at least in a working movement.

4. The surgical instrument as claimed in claim 1, wherein a locking device is provided for exerting a locking force between the control elements.

5. The surgical instrument as claimed in claim 1, wherein the locking device, in one operating state, is secured to the control elements in such a way as to be separable, without use of tools, for cleaning and/or disinfection.

6. The surgical instrument as claimed in claim 1, wherein the connecting device has at least one unlocking control means, which is at least partially arranged on a side of the control unit, which side faces away from the control elements.

7. The surgical instrument as claimed in claim 1, wherein
the shaft and the push-pull element are movable relative to each other, and
a connecting element connecting the shaft and the push-pull element to each other, and the connecting element connecting the shaft and the push-pull element on the side of the shaft and preventing the push-pull element from pivoting relative to the shaft and releasing the push-pull element from the shaft,
wherein the connecting element is formed at least partially by a spring.

8. The surgical instrument as claimed in claim 7, wherein the connecting element is firmly connected to the shaft and/or to the push-pull element.

9. The surgical instrument as claimed in claim 7, wherein the shaft and/or the push-pull element has an at least partially T-shaped groove which, in at least one operating state, at least partially guides the connecting element.

10. The surgical instrument as claimed in claim 7, wherein the push-pull element is mounted in such a way that it can be pivoted at least partially out of the shaft.

11. The surgical instrument as claimed in claim 2, wherein the control unit has a slotted guide, which guides the control elements at least in a working movement.

12. The surgical instrument as claimed in claim 2, wherein a locking device is provided for exerting a locking force between the control elements.

13. The surgical instrument as claimed in claim 3, wherein a first of the control elements has a joint axle and a second of the control elements has a recess into which the joint axle can be inserted by an operator when joining the control elements together.

14. The surgical instrument as claimed in claim 3, wherein the slotted guide has a working area and a pin which is arranged in the working area and prevents the control elements from being separable.

15. The surgical instrument as claimed in claim 1, wherein the first stop of the push-pull element of the working unit is connected operatively to one of the two control elements.

16. The surgical instrument as claimed in claim 1, wherein the first stop hooks onto an edge of one of two control elements.

17. A surgical instrument, comprising:
a control unit having a first control element and a second control element, the second control element having a recess provided for a swiveling bearing of the first control element, a working unit having a shaft and a push-pull element, the shaft of the working unit including a recess, and the push-pull element of the working unit including first and second stops, a connecting device detachably connecting the working unit and the control unit to each other, and the surgical instrument including the working unit, the control unit, the first and second control elements of the control unit and the connecting device being configured to assemble and disassemble manually and without the use of tools between an operating state ready for performing surgery and a disassembled state for cleaning, wherein in the operating state the working unit, the control unit, the first and second control elements of the control unit and the connecting device are assembled together into the surgical instrument for performing surgery, in the disassembled state the working unit and the control unit are dismantled and separated from each other and the first and second control elements are dismantled and separated from each other for cleaning, and the first stop of the push-pull element of the working unit is arranged together with the first and second control elements into a form-fit connection when assembled in the operating state, the form-fit connection limiting movement of the two control elements relative to each other to engage with the recess of the second control element and preventing the first and second control elements from becoming oriented relative to one another at an orientation permitting release of either of the first and second control elements from the form-fit connection, and wherein the form-fit connection includes the second stop of the push-pull element engaging the recess of the shaft and limiting a movement clearance of the push-pull element relative to the shaft in a main direction of the shaft.

* * * * *